(12) United States Patent
Mahadevan, Jr. et al.

(10) Patent No.: US 10,245,400 B2
(45) Date of Patent: Apr. 2, 2019

(54) HANDHELD PRESSURE SUPPORT SYSTEM FOR TREATING HYPERINFLATION

(71) Applicant: KONINKLIJKE PHILIPS N.V., Eindhoven (NL)

(72) Inventors: Anandi Mahadevan, Jr., Murrysville, PA (US); Robert William Murdoch, Kennesaw, GA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 526 days.

(21) Appl. No.: 14/651,831

(22) PCT Filed: Dec. 4, 2013

(86) PCT No.: PCT/IB2013/060629
§ 371 (c)(1),
(2) Date: Jun. 12, 2015

(87) PCT Pub. No.: WO2014/091367
PCT Pub. Date: Jun. 19, 2014

(65) Prior Publication Data
US 2015/0320955 A1    Nov. 12, 2015

Related U.S. Application Data

(60) Provisional application No. 61/736,713, filed on Dec. 13, 2012.

(51) Int. Cl.
*A61M 16/00*    (2006.01)
*A61M 15/00*    (2006.01)
(Continued)

(52) U.S. Cl.
CPC ...... *A61M 16/0069* (2014.02); *A61M 15/009* (2013.01); *A61M 16/0003* (2014.02);
(Continued)

(58) Field of Classification Search
CPC .... A61M 15/00; A61M 15/009; A61M 15/06; A61M 15/08; A61M 16/00;
(Continued)

(56) References Cited

U.S. PATENT DOCUMENTS

| 5,398,676 A | 3/1995 | Press |
| 6,355,002 B1 | 3/2002 | Faram |

(Continued)

FOREIGN PATENT DOCUMENTS

| FR | 2905275 A1 | 3/2008 |
| JP | 2905275 B2 | 6/1999 |

(Continued)

OTHER PUBLICATIONS

Machine translation of FR 2905275.*
(Continued)

*Primary Examiner* — Jackie Tan-Uyen T Ho
*Assistant Examiner* — Joseph D Boecker
(74) *Attorney, Agent, or Firm* — Michael W. Haas

(57) ABSTRACT

A portable handheld pressure support system (10) is configured to provide pressure support therapy to a subject. The pressure support system provides a pressurized flow of breathable gas that is delivered to the airway of the subject to treat COPD and/or dyspnea, hyperinflation, and/or other conditions. The system is configured to adjust an expiratory pressure level of the pressure support therapy responsive to identification of hyperinflation in the subject. The pressure support therapy provided to the subject is configured to be used as needed to rapidly alleviate shortness of breath, hyperinflation, and/or other symptoms. The pressure support system is configured to be small and lightweight so that the subject may carry the system and use the system as needed.

18 Claims, 3 Drawing Sheets

(51) Int. Cl.
*A61B 5/091* (2006.01)
*A61M 16/10* (2006.01)
*A61M 16/12* (2006.01)
*A61M 16/16* (2006.01)

(52) U.S. Cl.
CPC ...... *A61M 16/0057* (2013.01); *A61M 16/026* (2017.08); *A61B 5/091* (2013.01); *A61M 16/10* (2013.01); *A61M 16/106* (2014.02); *A61M 16/1055* (2013.01); *A61M 16/12* (2013.01); *A61M 16/161* (2014.02); *A61M 2016/0027* (2013.01); *A61M 2016/0039* (2013.01); *A61M 2016/0042* (2013.01); *A61M 2205/332* (2013.01); *A61M 2205/3303* (2013.01); *A61M 2205/3334* (2013.01); *A61M 2205/3368* (2013.01); *A61M 2205/50* (2013.01); *A61M 2205/586* (2013.01); *A61M 2205/82* (2013.01); *A61M 2205/8206* (2013.01); *A61M 2230/42* (2013.01)

(58) Field of Classification Search
CPC .......... A61M 16/0003; A61M 16/0051; A61M 16/0057; A61M 16/0069; A61M 16/021; A61M 16/022; A61M 16/024; A61M 16/10; A61M 16/12; A61M 2016/0027; A61M 2016/0033; A61M 2016/0039; A61M 2205/3303; A61M 2205/332; A61M 2205/3327; A61M 2205/3331; A61M 2205/3334; A61M 2205/3344; A61M 2205/50; A61M 2205/82; A61M 2205/8206; A61M 11/08; A61B 5/091
See application file for complete search history.

(56) References Cited

U.S. PATENT DOCUMENTS

| | | | | |
|---|---|---|---|---|
| 8,136,527 | B2* | 3/2012 | Wondka | A61M 16/06 128/200.24 |
| 8,375,944 | B2* | 2/2013 | Kwok | A61M 16/06 128/204.18 |
| 8,534,284 | B2 | 9/2013 | Dunsmore | |
| 9,750,907 | B2* | 9/2017 | Librett | A61M 16/0066 |
| 9,956,132 | B2* | 5/2018 | Francois | A61N 1/3601 |
| 2004/0249300 | A1 | 12/2004 | Miller | |
| 2005/0031322 | A1 | 2/2005 | Boyle | |
| 2005/0051168 | A1 | 3/2005 | DeVries | |
| 2007/0045152 | A1* | 3/2007 | Kwok | A61M 16/00 206/733 |
| 2007/0169781 | A1* | 7/2007 | Tang | A61M 16/00 128/206.21 |
| 2011/0067698 | A1* | 3/2011 | Zheng | A61M 16/20 128/204.25 |
| 2011/0203587 | A1 | 8/2011 | Bertinetti | |
| 2012/0118290 | A1 | 5/2012 | Sinderby | |
| 2012/0152255 | A1* | 6/2012 | Barlow | A61M 16/0066 128/205.25 |
| 2013/0118498 | A1* | 5/2013 | Robitaille | A61M 16/0075 128/205.16 |
| 2014/0299130 | A1* | 10/2014 | Librett | A61M 16/0066 128/204.18 |
| 2014/0299132 | A1* | 10/2014 | Librett | A61M 16/0066 128/205.25 |
| 2014/0299133 | A1* | 10/2014 | Neely | B65H 75/40 128/205.25 |
| 2014/0299406 | A1* | 10/2014 | Librett | A61M 16/0816 181/224 |
| 2015/0128947 | A1* | 5/2015 | Mahadevan | A61M 16/00 128/204.21 |
| 2015/0136129 | A1* | 5/2015 | Mahadevan | A61M 15/009 128/203.14 |
| 2015/0283339 | A1* | 10/2015 | Mahadevan | A61M 15/009 128/203.14 |
| 2015/0313535 | A1* | 11/2015 | Alshaer | A61B 5/4812 600/529 |

FOREIGN PATENT DOCUMENTS

| | | |
|---|---|---|
| JP | 2002011099 A | 1/2002 |
| JP | 2007501074 A | 1/2007 |
| JP | 2008540062 A | 11/2008 |
| JP | 2010509004 A | 3/2010 |
| JP | 2012505691 A | 3/2012 |
| RU | 2185196 C2 | 7/2002 |
| WO | WO2006127573 A2 | 11/2006 |
| WO | WO2010044038 A2 | 4/2010 |
| WO | WO2013160822 A1 | 10/2012 |
| WO | WO2013179173 A1 | 12/2013 |

OTHER PUBLICATIONS

"SleepWeaver Feather Weight Tube", retrieved from https://web.archive.org/web/20120226150111/https://www.cpap.com/productpage/circadiance-sleepweaver-feather-weight-cpap-tube.html with date Feb. 26, 2012.*

"Tenergy Li-Ion 18650 14.8V 2200mAh Rechargeable Battery Pack w/ PCB Protection", retrieved from https://web.archive.org/web/20120306060201/http://www.all-battery.com:80/li-ion18650148v2 200mahrechargeablebatterypackwithpcbprotection.aspx with date Mar. 6, 2012.*

"HDM Z1 Travel CPAP Machine with Z-Breathe#", retrieved from https://www.cpapdirect.com/cpap-machines/hdm-z1-travel-cpap-machine-with-z-breathe.*

* cited by examiner

HANDHELD PRESSURE SUPPORT SYSTEM FOR TREATING HYPERINFLATION

CROSS-REFERENCE TO RELATED APPLICATIONS

This patent application claims the priority benefit under 35 U.S.C. § 371 of international patent application no. PCT/IB2013/060629, filed Dec. 44, 2013, which claims the priority benefit under 35 U.S.C. § 119(e) of U.S. Provisional Application No. 61/736,713, filed on Dec. 13, 2012, the contents of which are herein incorporated by reference.

BACKGROUND OF THE INVENTION

1. Field of the Invention

The present disclosure pertains to a portable handheld pressure support system configured to deliver a pressurized flow of breathable gas to the airway of a subject.

2. Description of the Related Art

A positive air pressure (PAP) can be applied to a patient's airway to keep the airway open and avoid collapse during breathing. This positive pressure effectively "splints" the airway, thereby maintaining an open passage to the lungs. Dyspnea, or shortness of breath, is a primary symptom of chronic obstructive pulmonary disease (COPD). COPD patients may also experience hyperinflation. COPD patients suffer occurrences of dyspnea and/or hyperinflation when exerting themselves. The forms of exertion may include, for example, performing household chores, walking to the local store, or climbing a set of stairs. An onset of dyspnea may limit a patient's ability to perform activities and can trigger apprehension or panic, further reducing the patient's ability to function. Some COPD patients carry short acting bronchodilators to alleviate their symptoms of dyspnea. Bronchodilators are steroid based, typically require 4-20 minutes to act, are mostly effective for only asthmatic-based symptoms, and rely on expensive pharmaceuticals.

SUMMARY OF THE INVENTION

Accordingly, one or more aspects of the present disclosure relate to a portable handheld pressure support system configured to deliver a pressurized flow of breathable gas to the airway of a subject. The pressure support system comprises a pressure generator, a subject interface, one or more sensors, one or more processors, a portable power system, a housing, and a handle. The pressure generator is configured to generate the pressurized flow of breathable gas. The subject interface is configured to communicate the pressurized flow of breathable gas to the airway of the subject. The one or more sensors are configured to generate output signals conveying information related to one or more gas parameters of the pressurized flow of breathable gas. The one or more processors are configured to execute computer program modules. The computer program modules comprise a control module, a hyperinflation module, and an expiratory pressure module. The control module is configured to control operation of the pressure generator to generate the pressurized flow of breathable gas based on the output signals from the one or more sensors according to a positive pressure support therapy regime. The positive pressure support therapy regime dictates an inspiratory pressure level and an expiratory pressure level. The hyperinflation module is configured to identify hyperinflation during exhalation based on the output signals. The expiratory pressure module is configured to control the pressure generator to adjust, responsive to identification of hyperinflation by the hyperinflation module, the expiratory pressure level to relieve hyperinflation during exhalation. The portable power system is configured to power the pressure generator, the one or more sensors, and the one or more processors. The housing is configured to contain the pressure generator, the subject interface, the one or more sensors, the one or more processors, and the power system. The handle is attached to and/or formed by the housing and is configured to be grasped by the subject to hold the housing in position with respect to the airway of the subject as the pressurized flow of breathable gas is delivered to the airway of the subject.

Yet another aspect of the present disclosure relates to a method of delivering a pressurized flow of breathable gas to the airway of a subject with a handheld pressure support system. The handheld pressure support system includes a housing. The housing contains a pressure generator, a subject interface, one or more sensors, a power system, and one or more processors. The one or more processors are configured to execute computer program modules. The computer program modules include a control module, a hyperinflation module, and an expiratory pressure module. The housing forms and/or is attached to a handle. The method comprises generating the pressurized flow of breathable gas with the pressure generator; communicating the pressurized flow of breathable gas to the airway of the subject with the subject interface; generating output signals conveying information related to one or more gas parameters of the pressurized flow of breathable gas with the one or more sensors; controlling, with the control module, generation of the pressurized flow of breathable gas based on the output signals from the one or more sensors according to a positive pressure support therapy regime, the positive pressure support therapy regime dictating an inspiratory pressure level and an expiratory pressure level; identifying hyperinflation during exhalation with the hyperinflation module, based on the output signals; controlling the pressure generator to adjust, with the expiratory pressure module, responsive to identification of hyperinflation during exhalation, the expiratory pressure level to relieve hyperinflation during exhalation; portably powering the pressure generator, the one or more sensors, the valve, and the one or more processors with the power system; and engaging the hand of the user with the handle, the handle configured such that the housing is held in position with respect to the airway of the subject as the pressurized flow of breathable gas is delivered to the airway of the subject.

Still another aspect of the present disclosure relates to a portable handheld pressure support system configured to deliver a pressurized flow of breathable gas to the airway of a subject. The pressure support system comprises means for generating the pressurized flow of breathable gas; means for communicating the pressurized flow of breathable gas to the airway of the subject; means for generating output signals conveying information related to one or more gas parameters of the pressurized flow of breathable gas; and means for executing computer program modules. The computer program modules comprise means for controlling operation of the means for generating the pressurized flow of breathable gas to generate the pressurized flow of breathable gas based on the output signals from the means for generating output signals according to a positive pressure support therapy regime, the positive pressure support therapy regime dictating an inspiratory pressure level and an expiratory pressure level; means for identifying hyperinflation during exhalation based on the output signals; and means for controlling the means for generating the pressurized flow of breathable gas to adjust, responsive to identification of hyperinflation by the means for identifying, the expiratory pressure level to relieve hyperinflation during exhalation. The pressure support system further comprises means for portably powering the means for generating the pressurized flow of breathable gas, the means for generating output signals, and the means for executing computer program modules; means for containing the means for generating the pressurized flow of breathable gas, the means for communicating, the means for generating output signals, the means for executing computer program modules, and the means for portably powering; and means for engaging the hand of the subject to be grasped by the subject, the means for engaging being connected to and/or formed by the means for containing, the means for engaging being configured to be grasped by the subject to hold the means for containing in position with respect to the airway of the subject as the pressurized flow of breathable gas is delivered to the airway of the subject.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
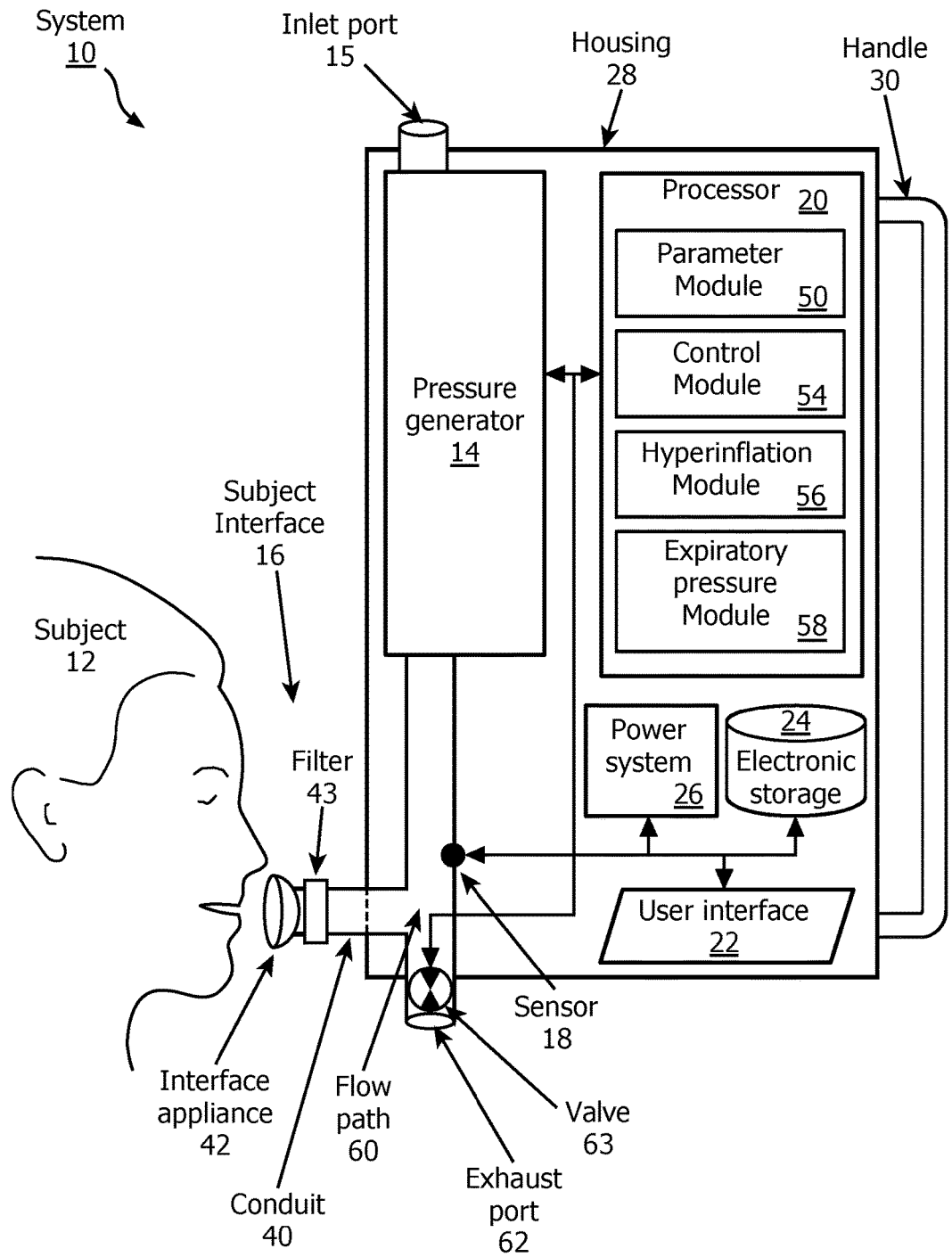
FIG. 1 is a schematic of a portable handheld pressure support system configured to deliver a pressurized flow of breathable gas to the airway of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a portable handheld pressure support system 10 configured to provide pressure support therapy to a subject 12. Pressure support system 10 is configured to provide the pressure support therapy in the form of a pressurized flow of breathable gas that is delivered to the airway of subject 12. Pressure support system 10 is configured to treat COPD and/or other patients suffering from dyspnea, hyperinflation, and/or other conditions. System 10 is configured to adjust an expiratory pressure level of the pressure support therapy responsive to identification of hyperinflation in subject 12. The pressure support therapy provided to subject 12 is configured to be used as needed (e.g., intermittently) by subject 12 to rapidly alleviate shortness of breath, hyperinflation, and/or other symptoms. Pressure support system 10 is configured to be small and lightweight so that subject 12 may carry system 10 and use system 10 as needed without requiring a device to be worn on the face. The present disclosure contemplates that portable handheld pressure support system 10 may be used to treat symptoms and/or conditions related to dyspnea and/or hyperinflation due to COPD, and/or for other uses. The other uses may include, for example, treating dyspnea related to pulmonary cancer, treating emphysema, treating pneumonia, treating Cheyne-Stokes respiration and/or other disordered breathing, improving the exercise capacity of any patient limited by dyspnea and/or hyperinflation, and/or other uses.

Examples of similar portable handheld pressure support systems are described in U.S. Patent Application No. 61/637,586 filed Apr. 24, 2012, entitled "Portable Handheld Pressure Support System and Method", and/or U.S. Patent Application No. 61/653,052, filed May 30, 2012, entitled "Portable Handheld Blending Gas Enriched Pressure Support System and Method", the contents of both of which are incorporated herein by reference.

In some embodiments, system 10 comprises one or more of a pressure generator 14, a subject interface 16, one or more sensors 18, one or more processors 20, a user interface 22, electronic storage 24, a portable power system 26, a housing 28, a handle 30, and/or other components.

Pressure generator 14 is configured to generate a flow of gas for delivery to the airway of subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control an expiratory pressure level of the flow of gas during and exhalation of the patient to provide pressure support to the airway of subject 12.

Pressure generator 14 receives a flow of gas from a gas source, such as the ambient atmosphere, and elevates the pressure of that gas for delivery to the airway of a patient. In some embodiments, pressure generator 14 receives a flow of gas from a gas source through inlet port 15. Pressure generator 14 is any device, such as, for example, a pump, blower, piston, or bellows, that is capable of elevating the pressure of the received gas for delivery to a patient or generating a flow of gas. Pressure generator 14 may comprise one or more valves for controlling the pressure/flow of gas. The present disclosure also contemplates controlling the operating speed of the blower, either alone or in combination with such valves, to control the pressure/flow of gas provided to the patient.

In some embodiments, pressure generator 14 may be configured to supply a pressurized flow of breathable gas at pressures between about 1 cm of water and about 40 cm of water. In some embodiments, pressure generator 14 may be configured to supply a pressurized flow of breathable gas at pressures between 2 cm of water and about 30 cm of water.

Subject interface 16 is configured to communicate the pressurized flow of breathable gas to the airway of subject 12. As such, subject interface 16 comprises conduit 40, interface appliance 42, filter 43, and/or other components. In some embodiments, filter 43 is configured to filter bacteria and/or other materials. Conduit 40 is configured to convey the pressurized flow of gas to interface appliance 42. Interface appliance 42 is configured to deliver the flow of gas to the airway of subject 12. In some embodiments, interface appliance 42 is configured to be non-invasively engaged by the mouth of subject 12. Non-invasive engagement comprises removably engaging one or more external orifices of the airway of subject 12 (e.g., nostrils and/or mouth) to communicate gas between the airway of subject 12 and interface appliance 42.

In some embodiments, interface appliance 42 is removably coupled to conduit 40. Interface appliance 42 may be removed for cleaning and/or for other purposes. In some embodiments, conduit 40 is configured as a mouthpiece to be engaged by the mouth of subject 12.

In some embodiments, other non-invasive interface appliances may be configured as interface appliance 42. Some examples of non-invasive interface appliance 42 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance. In some embodiments, system 10 may be connected to a classical respiratory circuit (e.g., a six foot hose) such that the classical respiratory circuit functions as subject interface 16.

One or more sensors 18 are configured to generate output signals conveying information related to one or more parameters of the gas within system 10. The one or more parameters of the gas within system 10 may comprise gas parameters related to the pressurized flow of breathable gas, breathing parameters related to respiration of subject 12, and/or other parameters. Sensors 18 may comprise one or more sensors that measure such parameters directly (e.g., through fluid communication with the flow of gas in interface appliance 42). Sensors 18 may comprise one or more sensors that generate output signals related to the one or more parameters indirectly. For example, sensors 18 may comprise one or more sensors configured to generate an output based on an operating parameter of pressure generator 14 (e.g., patient flow and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, peak inhaled and exhaled flows, peak inspiratory and expiratory pressures, and/or other gas parameters. Breathing parameters related to the respiration of subject 12 may comprise a tidal volume, an expiratory flow limitation, a timing (e.g., beginning and/or end of inhalation, beginning and/or end of exhalation, etc.), a respiration rate, a duration (e.g., of inhalation, of exhalation, of a single breathing cycle, etc.), respiration frequency, peak inhaled and exhaled flows, peak inspiratory and expiratory pressures, and/or other breathing parameters.

Although sensors 18 are illustrated in FIG. 1 at a single location in system 10, this is not intended to be limiting. Sensors 18 may comprise sensors disposed in a plurality of locations, such as for example, at various locations within (or in communication with) conduit 40, within pressure generator 14, within (or in communication with) interface appliance 42, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a parameter module 50, a control module 54, a hyperinflation module 56, an expiratory pressure module 58, and/or other modules. Processor 20 may be configured to execute modules 50, 54, 56, and/or 58 by software; hardware; firmware; some combination of software, hardware, and/or firmware; and/or other mechanisms for configuring processing capabilities on processor 20.

It should be appreciated that although modules 50, 54, 56, and 58 are illustrated in FIG. 1 as being co-located within a single processing unit, in embodiments in which processor 20 comprises multiple processing units, one or more of modules 50, 54, 56, and/or 58 may be located remotely from the other modules. The description of the functionality provided by the different modules 50, 54, 56, and/or 58 described below is for illustrative purposes, and is not intended to be limiting, as any of modules 50, 54, 56, and/or 58 may provide more or less functionality than is described. For example, one or more of modules 50, 54, 56, and/or 58 may be eliminated, and some or all of its functionality may be provided by other modules 50, 54, 56, and/or 58. As another example, processor 20 may be configured to execute one or more additional modules that may perform some or all of the functionality attributed below to one of modules 50, 54, 56, and/or 58.

Parameter module 50 is configured to determine one or more parameters within system 10. The one or more parameters within system 10 may comprise gas parameters related to the pressurized flow of breathable gas, breathing parameters related to the respiration of subject 12, and/or other parameters. Parameter module 50 is configured to determine the one or more parameters based on the output signals of sensors 18. The information determined by parameter module 50 may be used for controlling pressure generator 14, stored in electronic storage 24, and/or used for other uses.

The one or more parameters determined by parameter module 50 may include, for example, one or more of a flow rate, a volume, a pressure, humidity, temperature, acceleration, velocity, a tidal volume, an expiratory flow limitation, a timing (e.g., beginning and/or end of inhalation, beginning and/or end of exhalation, etc.), a respiration rate, a duration (e.g., of inhalation, of exhalation, of a single breathing cycle, etc.), respiration frequency, peak flows, peak pressures, and/or other parameters.

Control module 54 is configured to control pressure generator 14 to generate the flow of gas in accordance with a positive pressure support therapy regime. In some embodiments, the positive pressure support therapy regime dictates an inspiratory pressure level and an expiratory pressure level. In positive airway pressure support therapy the pressurized flow of gas generated by the pressure generator is controlled to replace and/or compliment a patient's regular breathing. Positive airway pressure support therapy may be used to maintain an open airway in a patient so that oxygen and carbon dioxide may be exchanged more easily, requiring little and/or no effort from the patient. By way of non-limiting example, control module 54 may control pressure generator 14 such that the pressure support provided to the subject via the flow of gas comprises bi-level positive pressure airway support (BiPAP), proportional positive airway pressure support (PPAP), forced oscillation technique, and/or other types of pressure support therapy.

BiPAP provides a first inspiratory pressure (IPAP) and a second, typically lower, expiratory pressure (EPAP) for easier exhalation during ventilation. In some therapy modes (e.g., PPAP), control module 54 may control pressure generator 14 to apply variable pressure support in which the amount of pressure delivered to the patient during inhalation and/or during exhalation is determined and delivered on a breath by breath basis. In some embodiments, control module 54 is configured to control pressure generator 14 to supply a positive end expiratory pressure (PEEP) to subject 12. The PEEP will help maintain the airway patency. The PEEP level may be adjusted to a value to overcome an intrinsic peep level to provide optimal ventilation to the patient. Optimal ventilation includes maintaining optimal blood oxygen saturation levels and being able to exhale CO2. In some embodiments, an EPAP level and a PEEP level may be similar and/or the same.

Control module 54 is configured to control pressure generator 14 based on information related to the output signals from sensors 18, information determined by parameter module 50, information entered by a user to user interface 22, information determined by control module 54 based on previous respiration of subject 12, and/or based on other information.

Hyperinflation module 56 is configured to identify hyperinflation during exhalation based on the output signals. Hyperinflation module 56 may identify hyperinflation based on information conveyed by the output signals from sensors 18, parameter information (e.g., breathing parameter information) determined by parameter module 50, and/or other information. For example, hyperinflation module 56 may identify hyperinflation based on information related to a tidal volume, an expiratory flow limitation (e.g., indicated by an expiratory flow rate), a pressure in the lungs of subject 12 at the end of exhalation, and/or other parameters determined by parameter module 50 for one or more breaths by subject 12. In some embodiments, hyperinflation module 56 may be configured to identify hyperinflation based on an analysis by hyperinflation module 56 of the information conveyed by the output signals from sensors 18, the information determined by parameter module 50, and/or other information. For example, hyperinflation module 56 may be configured to compare a first pressure in the lungs at the end of a first exhalation to a second pressure in the lungs at the end of a second exhalation to identify air trapping in the lungs of subject 12.

Many COPD patients suffer from airflow obstruction, which leads to incomplete expiration. During exertion, patients with emphysema may experience a significant amount of air trapping, which leads to dynamic hyperinflation with auto-peak end-expiratory pressure phenomenon. Hyperinflation due to incomplete lung emptying, especially with exercise, may lead to a further increase in intra-alveolar pressure and decreased inspiratory capacity. The increased resistance to airflow and higher ventilatory demand, is what causes dynamic hyperinflation and increases the work of breathing. External PEEP in these cases may be used to decrease the work of breathing and relieve dyspnea in patients with COPD.

Expiratory pressure module 58 is configured to control pressure generator 14 to adjust an expiratory pressure level of the pressurized flow of breathable gas to relieve hyperinflation during exhalation. Expiratory pressure module 58 is configured to control pressure generator 14 to adjust an expiratory pressure level responsive to identification of hyperinflation by hyperinflation module 56. In some embodiments, the expiratory pressure level is a PEEP level. In some embodiments, expiratory pressure module 58 may be configured to control pressure generator 14 to adjust the positive end expiratory pressure level to reduce and/or eliminate an expiratory flow limitation and/or to provide positive pressure support therapy to relieve symptoms of dyspnea.

In some embodiments, expiratory pressure module 58 is configured to control pressure generator 14 to increase and/or decrease the PEEP level to reduce and/or eliminate hyperinflation. Whether the PEEP level is increased and/or decreased is determined by expiratory pressure module 58 based on information conveyed by the output signals from sensors 18, parameter information from parameter module 50 (e.g., information related to a tidal volume, an expiratory flow rate that indicates a flow limitation, a pressure at the end of exhalation), and/or other information. For example, expiratory pressure module 58 may be configured to control pressure generator 14 to increase the PEEP level responsive to the information described above indicating hyperinflation, and reduce the PEEP level responsive to the information described above indicating no hyperinflation, and/or indicating reduced hyperinflation.

In some embodiments, the increase and/or decrease in the PEEP level is proportional to a level of hyperinflation determined by expiratory pressure module 58. The level of hyperinflation may be determined by expiratory pressure module 58 based on information conveyed by the output signals from sensors 18, parameter information from parameter module 50, and/or other information. By way of a non-limiting example, expiratory pressure module 58 may be configured to control pressure generator 14 to increase the PEEP level by delivered to subject 12 by a relatively large amount responsive to determining a relatively high level of hyperinflation in subject 12. Expiratory pressure module 58 may be configured to control pressure generator 14 to increase the PEEP level by delivered to subject 12 by a relatively small amount responsive to determining a relatively low level of hyperinflation in subject 12. In some embodiments, expiratory pressure module 58 may be configured to control pressure generator 14 to decrease and/or leave the PEEP level unchanged responsive to determining a relatively low level of, and/or no hyperinflation in subject 12.

In some embodiments, expiratory pressure module 58 is configured to adjust the PEEP level based on information conveyed by the output signals from sensors 18, parameter information from parameter module 50, and/or other information determined during a single exhalation of subject 12. In some embodiments, expiratory pressure module 58 is configured to adjust the PEEP level based on information conveyed by the output signals from sensors 18, parameter information from parameter module 50, and/or other information determined during a series of one or more exhalations of subject 12 (e.g., an average of one or more breathing parameters).

In some embodiments, expiratory pressure module 58 may be configured to control pressure generator 14 to adjust the PEEP pressure level in proportion to the level of hyperinflation determined by expiratory pressure module 58 based on information determined from an algorithm. Expiratory pressure module 58 may determine the adjusted (e.g., increased and/or decreased) PEEP pressure level based on the algorithm. The algorithm may be determined at manufacture, determined by expiratory pressure module 58 based on information entered by subject 12 and/or other users (e.g., a doctor, a caregiver) via user interface 22, and/or determined by other methods.

Expiratory pressure module 58 may be configured to determine algorithm inputs based on lung resistance and/or reactance information. Lung resistance and/or reactance information may comprise information that describes the resistance of the airway of subject 12 to airflow during inspiration and/or expiration. Expiratory pressure module 58 may be configured to determine lung resistance and/or reactance information responsive to control module 54 controlling pressure generator 14 according to the forced oscillation technique. Expiratory pressure module 58 may be configured to determine algorithm inputs based on outputs from sensors 18 and/or parameter module 50 while control module 54 controls pressure generator 14 according to the forced oscillation technique. In some embodiments, algorithm inputs may be determined by expiratory pressure module 58 based on information from sensors 18 and/or parameter module 50 related to an inspiratory flow, changes in a peak expiratory flow, changes in an expiratory volume, and/or other information. In some embodiments, the algorithm may utilize one or more statistical techniques (e.g., least mean squares).

In some embodiments, the PEEP level may be increased and/or decreased by a predetermined amount of pressure. The predetermined amount of pressure may be determined at manufacture, set by subject 12 and/or other users (e.g., a doctor, a caregiver) via user interface 22, determined by expiratory pressure module 58 specifically for subject 12 based on previous respiration of subject 12 and/or other respiratory characteristics of subject 12 (e.g., a lung capacity of subject 12), and/or determined by other methods.

User interface 22 is configured to provide an interface between system 10 and subject 12, and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, processor 20, and/or other components of system 10. For example, therapy pressures, the breath rate of subject 12, the portable power system energy level, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with housing 28.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Information determined by processor 20 and/or stored by electronic storage 24 may comprise information related to an expiratory pressure level, respiration of subject 12, use frequency, and/or other information. The information stored by electronic storage 24 may be viewed via user interface 22, by connecting (wired and/or wireless) to a separate computer, and/or other via other methods. The information stored by electronic storage 24 may be used, for example, to adjust settings, to make adjustments to power system 26, used by a doctor to make medical decisions, and/or for other uses. In some embodiments, system 10 may include a wireless transmitter (not shown) and the information determined by processor 20, the information stored by electronic storage 24, and/or other information may be communicated to a care giver, for example, over a wireless network. By way of a non-limiting example, the care giver may receive use information, patient status, and/or other information, allowing the care giver to remotely track the therapy delivered by system 10.

Portable power system 26 is configured to power pressure generator 14, one or more sensors 18, one or more processors 20, user interface 22, electronic storage 24, and/or other components of system 10 in a portable manner. Power system 26 may comprise one or more power sources. The one or more power sources may be connected in series and/or in parallel. In some embodiments, the one or more power sources may not be connected. The one or more power sources may be configured to power one or more of the other components of system 10. In some embodiments, power system 26 is rechargeable. Power system 26 may be recharged via a home AC power source, a car battery outlet, an airplane power outlet, a USB port, a non-contact charging circuit, and/or other recharging methods. In some embodiments, portable power system 26 may supply up to 10V. In some embodiments, portable power system 26 may supply up to 15V. In some embodiments, portable power system 26 may supply up to 20V. Examples of portable power sources that may be included in portable power system 26 include one or more DC batteries, Lithium Ion and/or Lithium Polymer Cells, Nickel Metal Hydride, and/or other portable power sources. In some embodiments, portable power system 26 is configured to power system 10 for 10 or more hours of use. In some embodiments, portable power system 26 is configured to power system 10 for up to 10 hours of use. In some embodiments, portable power system 26 is configured to power system 10 for up to 8 hours of use. In some embodiments, portable power system 26 is configured to power system 10 for up to 6 hours of use.

Housing 28 is configured to contain pressure generator 14, subject interface 16, one or more sensors 18, one or more processors 20, user interface 22, electronic storage 24, power system 26, a flow path 60, an exhaust port 62, handle 30, and/or other components of system 10. Housing 28 is configured to contain the components of system 10 in a space small enough to be handheld and portable so pressure support therapy may be delivered at any time during the normal daily activities of subject 12. In some embodiments, the weight of system 10 is up to three pounds. In some embodiments, the weight of system 10 is up to two pounds. In some embodiments, the weight of system 10 is up to one pound. In some embodiments, the volume of housing 28 is up to 135 cubic inches. In some embodiments, the volume of housing 28 is up to 100 cubic inches. In some embodiments, the volume of housing 28 is up to 60 cubic inches.

Flow path 60 is configured to place subject interface 16 in fluid communication with pressure generator 14 and/or exhaust port 62. Exhaust port 62 is configured to direct exhaled gas from flow path 60 and/or pressure generator 14 to the ambient atmosphere. In some embodiments, flow through exhaust port 62 may be controlled by a valve 63. Valve 63 may be controlled by processor 20 to close during inhalation of subject 12 and open during exhalation. By way of a non-limiting example, control module 54 may control valve 63 to open and/or close based on one or more parameters determined by parameter module 50 (e.g., parameters indicating inhalation of subject 12 and/or exhalation of subject 12), and/or other information. In some embodiments, housing 28 may contain one or more additional ports (e.g., USB) configured to provide one or more connection points such that portable power system 26 may be recharged, electronic storage 24 may be accessed, and/or for other purposes.

Handle 30 is configured to be attached to and/or formed by housing 28. Handle 30 is configured to be grasped by subject 12 to hold the housing in position with respect to the airway of subject 12 as the pressurized flow of breathable gas is delivered to the airway of subject 12. Handle 30 may be attached to housing 28 by coupling handle 30 to housing 28 at one or more locations with screws and/or another method of fixing handle 30 to housing 28. Handle 30 may be formed in housing 28 by way of a ridged, knurled, and/or other textured surface. Handle 30 formed in housing 28 may comprise finger shaped surface depressions in housing 28 such that a user's fingers may fit into the finger depressions for gripping system 10. The method for mounting and/or the form factor for handle 30 formed by housing 28 described in the present disclosure is not intended to be limiting. Handle 30 may be attached to and/or formed in housing 28 by any method, in any shape, and/or in any location(s) that allows it to function as described herein.

Figure 2:
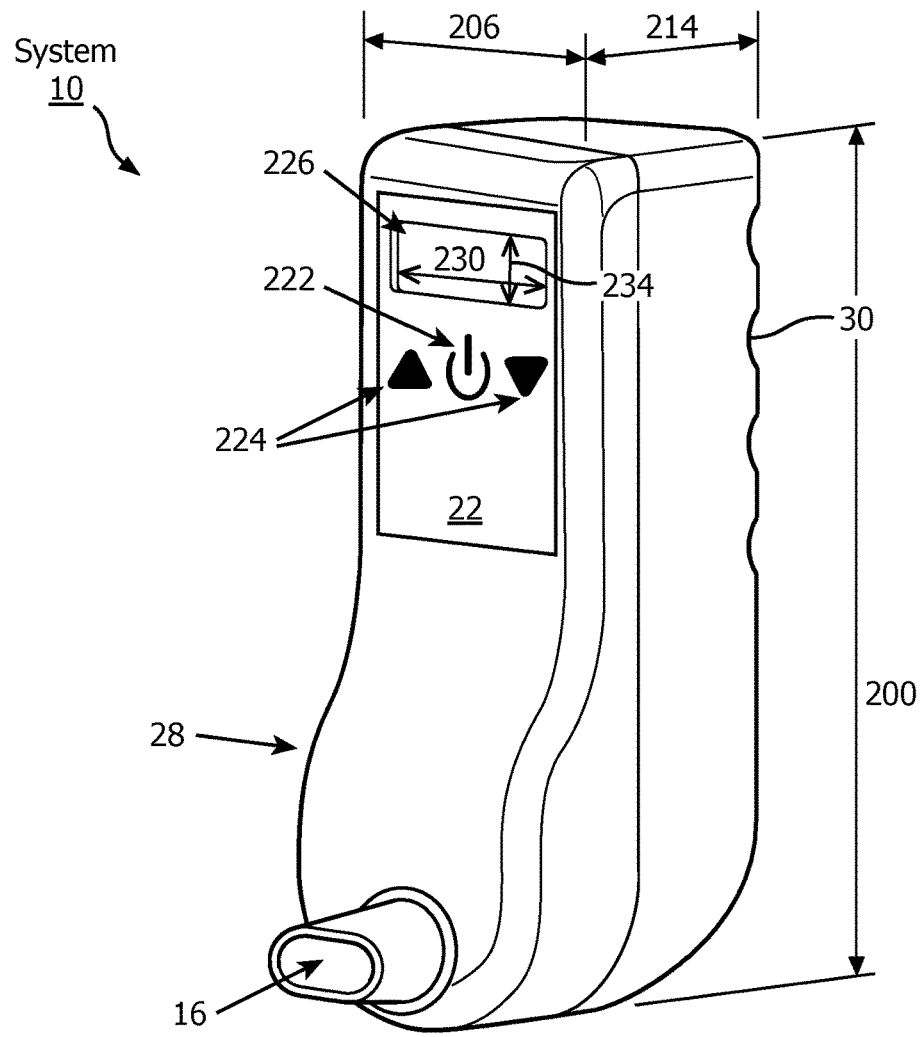
FIG. 2 is an example embodiment of the portable handheld pressure support system.
Figure 2:
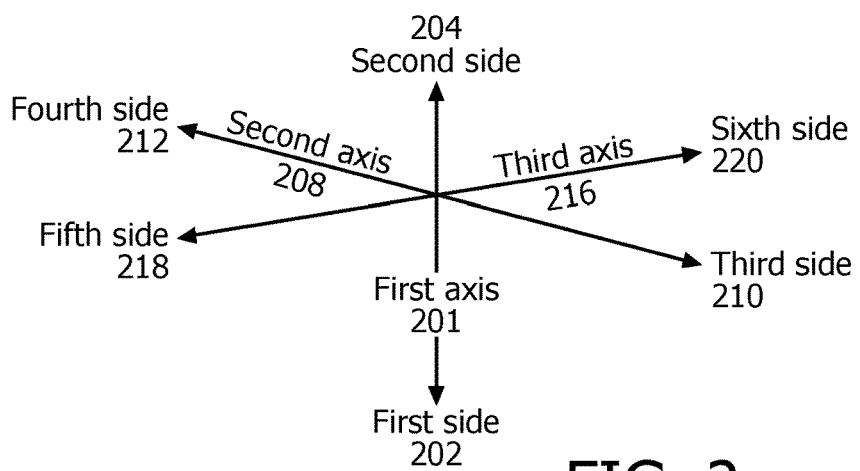

By way of a non-limiting example, FIG. 2 shows a perspective view of a possible embodiment of system 10. In this embodiment, housing 28 has a length 200 running along a first axis 201 from a first side 202 to a second side 204 of less than about 7 inches. Length 200 may be between about 5 inches and about 7 inches. Length 200 may be about 6 inches. In some embodiments, housing 28 may have a width 206 running along a second axis 208 from a third side 210 to a fourth side 212 of less than about 3 inches. Width 206 may be between about 2 inches and about 3 inches. Width 206 may be about 2.5 inches. Housing 28 has a thickness 214 running along a third axis 216 from a fifth side 218 toward a sixth side 220 of less than about 5 inches. Thickness 214 may be between about 4 inches and about 5 inches. Thickness 214 may be about 4.5 inches. The generally rectangular shape and approximate dimensions of housing 28 shown in FIG. 2 are not intended to be limiting. Housing 28 may take any shape that allows it to function as described in the present disclosure.

User interface 22 is also shown in FIG. 2. In example FIG. 2, user interface 22 is located on fifth side 218 and includes a power button 222, adjustment buttons 224, and a display 226. In this embodiment, display 226 has a width 230 running along second axis 208 from third side 210 to fourth side 212 of less than about 2 inches. Width 230 may be between about 1 inch and about 2 inches. Width 230 may be about 1.8 inches. Display 226 has a height 234 running along first axis 201 from first side 202 toward second side 204 of greater than about 0.5 inches. Height 234 may be between about 0.5 inches and about 1 inch. Height 234 may be about 0.6 inches.

Examples of subject interface 16 and handle 30 are also shown in FIG. 2. In FIG. 2, handle 30 is formed in housing 28 on sixth side 220 toward second side 204, opposite user interface 22. In FIG. 2, subject interface 16 is located on fifth side 218 (the same side as user interface 22) toward first side 202. Subject interface 16 is located in an area where thickness 214 increases along third axis toward fifth side 218 near first side 202.

Figure 3:
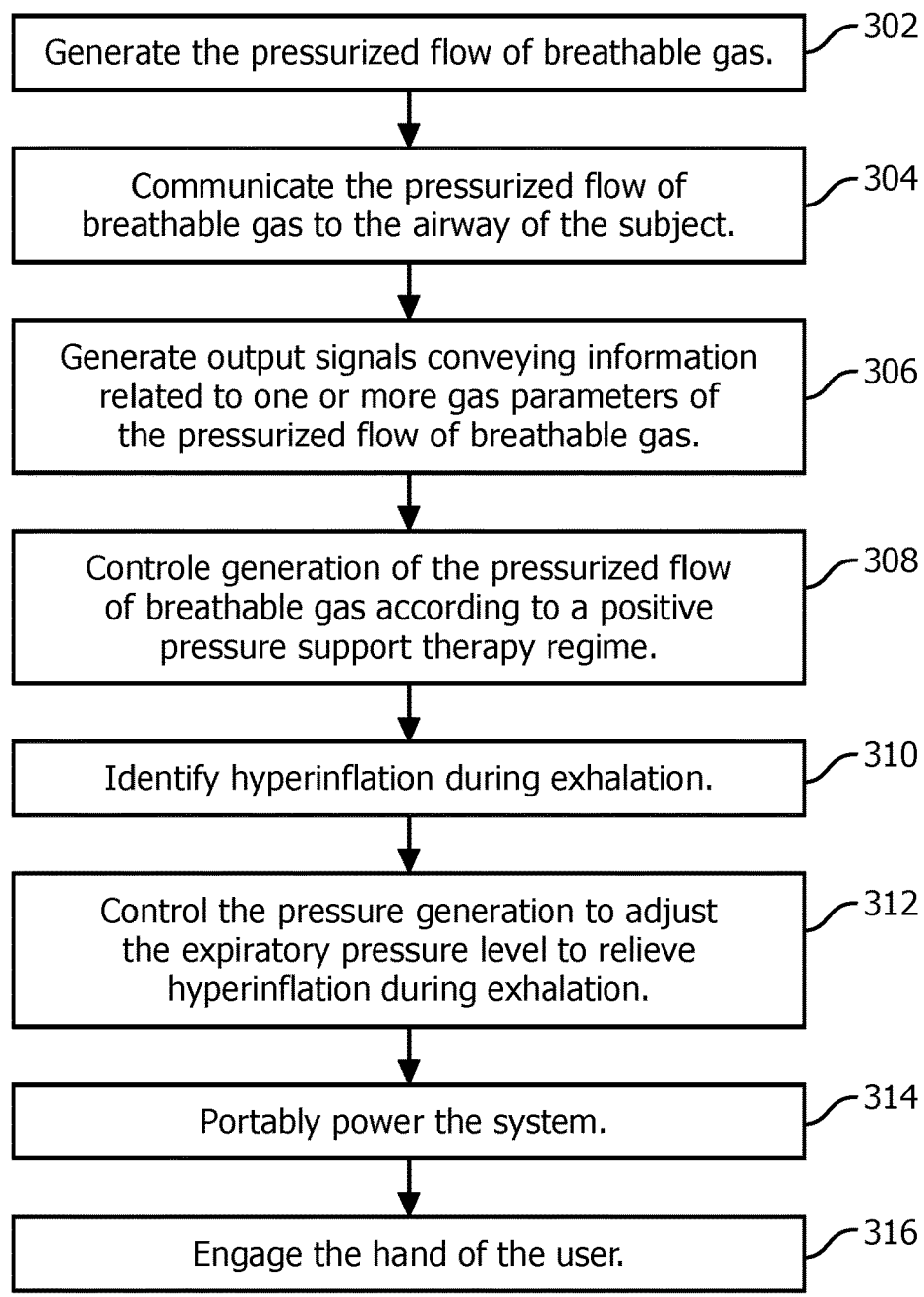
FIG. 3 is a method of delivering a pressurized flow of breathable gas to the airway of a subject.

FIG. 3 illustrates a method 300 of delivering a pressurized flow of breathable gas to the airway of a subject with a handheld pressure support system that includes a housing. The housing contains a pressure generator, a subject interface, one or more sensors, a power system, and one or more processors. The one or more processors are configured to execute computer program modules. The computer program modules include a control module, a hyperinflation module, and an expiratory pressure module. The housing forms and/or is attached to a handle. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, the pressurized flow of breathable gas is generated with the pressure generator. In some embodiments, operation 302 is performed by a pressure generator the same as or similar to pressure generator 14 (shown in FIG. 1 and described herein).

At an operation 304, the pressurized flow of breathable gas is communicated to the airway of the subject with the subject interface. In some embodiments, operation 304 is performed by a subject interface the same as or similar to subject interface 16 (shown in FIG. 1 and described herein).

At an operation 306, one or more output signals conveying information related to one or more gas parameters of the pressurized flow of breathable gas are generated with the one or more sensors. In some embodiments, operation 306 is performed by sensors the same as or similar to sensors 18 (shown in FIG. 1 and described herein.)

At an operation 308, the generation of the pressurized flow of breathable gas is controlled with the control module. The generation of the pressurized flow of breathable gas is controlled based on the output signals, according to a positive pressure support therapy regime. The positive pressure support therapy regime dictates an inspiratory pressure level and an expiratory pressure level. In some embodiments, operation 308 is performed by a control module the same as or similar to control module 54 (shown in FIG. 1 and described herein.)

At an operation 310, hyperinflation during exhalation is identified with the hyperinflation module. Hyperinflation is identified based on the output signals. In some embodiments, operation 310 is performed by a hyperinflation module the same as or similar to hyperinflation module 56 (shown in FIG. 1 and described herein.)

At an operation 312, the pressure generator is controlled with the expiratory pressure module to adjust the expiratory pressure level. The pressure generator is controlled to adjust the expiratory pressure level responsive to identification of hyperinflation during exhalation. The pressure generator is controlled to adjust the expiratory pressure level to relieve hyperinflation during exhalation. In some embodiments, operation 312 is performed by an expiratory pressure module the same as or similar to expiratory pressure module 58 (shown in FIG. 1 and described herein.)

At an operation 314, the pressure generator, the one or more sensors, and the one or more processors are powered with the portable power system. In some embodiments, operation 314 is performed by a portable power system the same as or similar to power system 26 (shown in FIG. 1 and described herein.)

At an operation 316, the hand of the user is engaged with the handle. The handle is configured such that the housing is held in position with respect to the airway of the subject as the pressurized flow of breathable gas is delivered to the airway of the subject. In some embodiments, operation 316 is performed by a handle the same as or similar to handle 30 (shown in FIG. 1 and described herein.)

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A portable handheld pressure support system configured to deliver a pressurized flow of breathable gas to the airway of a subject, the pressure support system comprising:
    (a) a pressure generator configured to generate the pressurized flow of breathable gas;
    (b) a subject interface configured to communicate the pressurized flow of breathable gas to the airway of the subject;
    (c) one or more sensors configured to generate output signals conveying information related to one or more gas parameters of the pressurized flow of breathable gas;
    (d) one or more processors configured to execute computer program modules, the computer program modules comprising:
        (1) a control module configured to control operation of the pressure generator to generate the pressurized flow of breathable gas based on the output signals from the one or more sensors according to a positive pressure support therapy regime, the positive pressure support therapy regime dictating an inspiratory pressure level and an expiratory pressure level,
        (2) a hyperinflation module configured to identify hyperinflation during exhalation based on the output signals, and
        (3) an expiratory pressure module configured to control the pressure generator to adjust, responsive to identification of hyperinflation by the hyperinflation module, the expiratory pressure level to relieve hyperinflation during exhalation;
    (e) a portable power system configured to power the pressure generator, the one or more sensors, and the one or more processors;
    (f) a housing configured to contain the pressure generator, the subject interface, the one or more sensors, the one or more processors, and the power system; and
    (g) a handle attached to and/or formed by the housing configured to be grasped by the subject to hold the housing in proximity to the mouth of the subject such that the subject interface contained by the housing is in position with respect to the mouth of the subject to be engaged by the mouth of the subject as the pressurized flow of breathable gas is delivered to the airway of the subject.

2. The pressure support system of claim 1, wherein the computer program modules further comprise a parameter module configured to determine one or more breathing parameters of the subject based on the output signals, the breathing parameters including one or more of a tidal volume, a flow rate, a pressure, a peak flow rate, a peak pressure, or an expiratory flow limitation, and wherein the hyperinflation module is configured to identify hyperinflation during exhalation based on the breathing parameters.

3. The pressure support system of claim 1, wherein a maximum volume of the housing is 135 cubic inches.

4. The pressure support system of claim 1, wherein the power system is configured to supply up to about 20V.

5. The pressure support system of claim 1, wherein a weight of the system is up to about 3 pounds.

6. The pressure support system of claim 1, wherein the handle is formed by the housing.

7. A method of delivering a pressurized flow of breathable gas to the airway of a subject with a handheld pressure support system that includes a housing, the housing containing a pressure generator, a subject interface, one or more sensors, a power system, and one or more processors, the one or more processors configured to execute computer program modules, the computer program modules including a control module, a hyperinflation module, and an expiratory pressure module, the housing forming and/or being attached to a handle, the method comprising:
generating the pressurized flow of breathable gas with the pressure generator;
communicating the pressurized flow of breathable gas to the airway of the subject with the subject interface;
generating output signals conveying information related to one or more gas parameters of the pressurized flow of breathable gas with the one or more sensors;
controlling, with the control module, generation of the pressurized flow of breathable gas based on the output signals from the one or more sensors according to a positive pressure support therapy regime, the positive pressure support therapy regime dictating an inspiratory pressure level and an expiratory pressure level;
identifying hyperinflation during exhalation with the hyperinflation module, based on the output signals;
controlling the pressure generator to adjust, with the expiratory pressure module, responsive to identification of hyperinflation during exhalation, the expiratory pressure level to relieve hyperinflation during exhalation;
portably powering the pressure generator, the one or more sensors, a valve, and the one or more processors with the power system; and
engaging a hand of the user with the handle, the handle configured such that the housing is held in proximity to the mouth of the subject such that the subject interface contained by the housing is in position with respect to the mouth of the subject to be engaged by the mouth of the subject as the pressurized flow of breathable gas is delivered to the airway of the subject.

8. The method of claim 7, further comprising determining one or more breathing parameters of the subject based on the output signals, the breathing parameters including one or more of a tidal volume, a flow rate, a pressure, a peak flow rate, a peak pressure, or an expiratory flow limitation, and wherein the hyperinflation identification during exhalation is based on the breathing parameters.

9. The method of claim 7, wherein a maximum volume of the housing is 135 cubic inches.

10. The method of claim 7, wherein the power system is configured to supply up to about 20V.

11. The method of claim 7, wherein a weight of the pressure support system is up to about 3 pounds.

12. The method of claim 7, further comprising forming the handle with the housing.

13. A portable handheld pressure support system configured to deliver a pressurized flow of breathable gas to the airway of a subject, the pressure support system comprising:
means for generating the pressurized flow of breathable gas;
means for communicating the pressurized flow of breathable gas to the airway of the subject;
means for generating output signals conveying information related to one or more gas parameters of the pressurized flow of breathable gas;
means for executing computer program modules, the computer program modules comprising:
(1) means for controlling operation of the means for generating the pressurized flow of breathable gas to generate the pressurized flow of breathable gas based on the output signals from the means for generating output signals according to a positive pressure support therapy regime, the positive pressure support therapy regime dictating an inspiratory pressure level and an expiratory pressure level,
(2) means for identifying hyperinflation during exhalation based on the output signals, and
(3) means for controlling the means for generating the pressurized flow of breathable gas to adjust, responsive to identification of hyperinflation by the means for identifying, the expiratory pressure level to relieve hyperinflation during exhalation;
means for portably powering the means for generating the pressurized flow of breathable gas, the means for generating output signals, and the means for executing computer program modules;
means for containing the means for generating the pressurized flow of breathable gas, the means for communicating, the means for generating output signals, the means for executing computer program modules, and the means for portably powering; and
means for engaging a hand of the subject to be grasped by the subject, the means for engaging being connected to and/or formed by the means for containing, the means for engaging being configured to be grasped by the subject to hold the means for containing in proximity to the mouth of the subject such that the means for communicating contained in the means for containing is in position with respect to the mouth of the subject to be engaged by the mouth of the subject as the pressurized flow of breathable gas is delivered to the airway of the subject.

14. The system of claim 13, wherein the computer program modules further comprise means for determining one or more breathing parameters of the subject based on the output signals, the breathing parameters including one or more of a tidal volume, a flow rate, a pressure, a peak flow rate, a peak pressure, or an expiratory flow limitation, and wherein the means for identifying hyperinflation is configured to identify hyperinflation during exhalation based on the breathing parameters.

15. The system of claim 13, wherein a maximum volume of the means for containing is 135 cubic inches.

16. The system of claim 13, wherein the means for portably powering is configured to supply up to about 20V.

17. The system of claim 13, wherein a weight of the system is up to about 3 pounds.

18. The system of claim 13, wherein the means for engaging is formed by the means for containing.

\* \* \* \* \*